US00PP12481P2

(12) United States Plant Patent
Fitch

(10) Patent No.: US PP12,481 P2
(45) Date of Patent: Mar. 19, 2002

(54) PAPAYA PLANT NAMED 'LAIE GOLD'

(75) Inventor: Maureen M. M. Fitch, Aiea, HI (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/444,769

(22) Filed: Nov. 22, 1999

(51) Int. Cl.[7] ..... A01H 5/00
(52) U.S. Cl. ..... Plt./156
(58) Field of Search ..... Plt./156

(56) References Cited

PUBLICATIONS

U.S. patent application Ser. No. 09/300,960, 'UH Rainbow'.
U.S. patent application Ser. No. 09/301,398, 'UH Sun Up'.

*Primary Examiner*—Bruce R. Campell
*Assistant Examiner*—Kent L. Bell
(74) *Attorney, Agent, or Firm*—Margaret A. Connor; M. Howard Silverstein; John D. Fado

(57) ABSTRACT

A new and distinct variety of papaya (*Carica papaya L.*) plant cv. 'Laie Gold' which is characterized by having the following combination of characteristics that are desirable in a new variety; large fruit size, high tree vigor, absence of occasional bitterness and unpleasant, strong odor during the cooler season, a lower incidence of carpellody and sterility, resistance to papaya ringspot virus, good fungus and nematode tolerance (good rooting capacity), early and low fruit bearing, and attractive globular pyriform fruit with delicate coconut- or mango-like taste and moderately firm flesh, giving good eating, handling, and shipping qualities.

4 Drawing Sheets

BACKGROUND OF THE INVENTION

1. Field of the Invention

The present invention relates to a new and distinct variety of papaya (*Carica papaya L.*) plant, which will hereinafter be denominated varietally as 'Laie Gold'. More particularly, the invention relates to the asexual propagation of *Carica papaya L.* cv. 'Laie Gold'. The new variety is a fresh market papaya for use in local markets as well as for long distance shipping.

2. Description of the Art

'Laie Gold' is an F1 (first generation) hybrid produced by crossing Hawaii's major large-fruited variety, 'Kamiya' (pollen parent, unpatented) with an unnamed plant from the F2 progeny (seed parent) of the hybrid papaya variety 'UH Rainbow' (U.S. Plant patent application Ser. No. 09/300,960) which has resistance to papaya ringspot virus (PRSV), an aphid-transmitted virus which is a major disease pathogen affecting papaya production worldwide. 'UH Rainbow' is an F1 hybrid produced by crossing Hawaii's standard export variety 'Kapoho' (unpatented) with a genetically engineered, PRSV-resistant papaya, 'UH SunUp' (U.S. Plant patent application Ser. No. 09/301,389), a red-fleshed papaya derived from the cultivar 'Sunset' (unpatented). The pollen parent 'Kamiya' grown in Waikane, Hi., is a selection of the University of Hawaii variety 'Waimanalo' (unpatented).

The first generation (F1) seedlings from an unnamed plant of 'UH Rainbow' F2×'Kamiya' crosses were grown in Laie, Kahaluu, and Waikane, Hi. Trees were measured monthly for trunk diameter, tree height, and height and date of first flowers. At fruiting, 9 months after transplanting to the fields, fruits were harvested monthly for one year to record sugar, firmness, weight, shape, flavor, and color.

The new hybrid variety of papaya plant has been asexually reproduced by both micropropagation and rooted cuttings at the U.S. Department of Agriculture-Agricultural Research Service/Hawaii Agriculture Research Center research laboratory and greenhouse in Aiea and Maunawili, Hi., respectively. Trees reproduced by both of these methods have shown that the characteristics run true to the original seedling trees. Fruit and tree characteristics are therefore transmitted through succeeding propagations.

SUMMARY OF THE INVENTION

The new variety cv. 'Laie Gold' may be distinguished from other commercial papaya cultivars known to me by a combination of characteristics, including larger fruit size, increased tree vigor, absence of occasional bitterness and unpleasant, strong odor during the cooler season, a lower incidence of carpellody and sterility, PRSV-resistance, good fungus and nematode tolerance (good rooting capacity), early and low fruit bearing, and attractive globular pyriform fruit with delicate coconut- or mango-like taste and moderately firm flesh, giving good eating, handling, and shipping qualities.

BRIEF DESCRIPTION OF THE DRAWINGS

The accompanying drawings are color photographs showing plants with trunks, leaves, and fruit of the new variety.

DETAILED BOTANICAL DESCRIPTION

Figure 1:
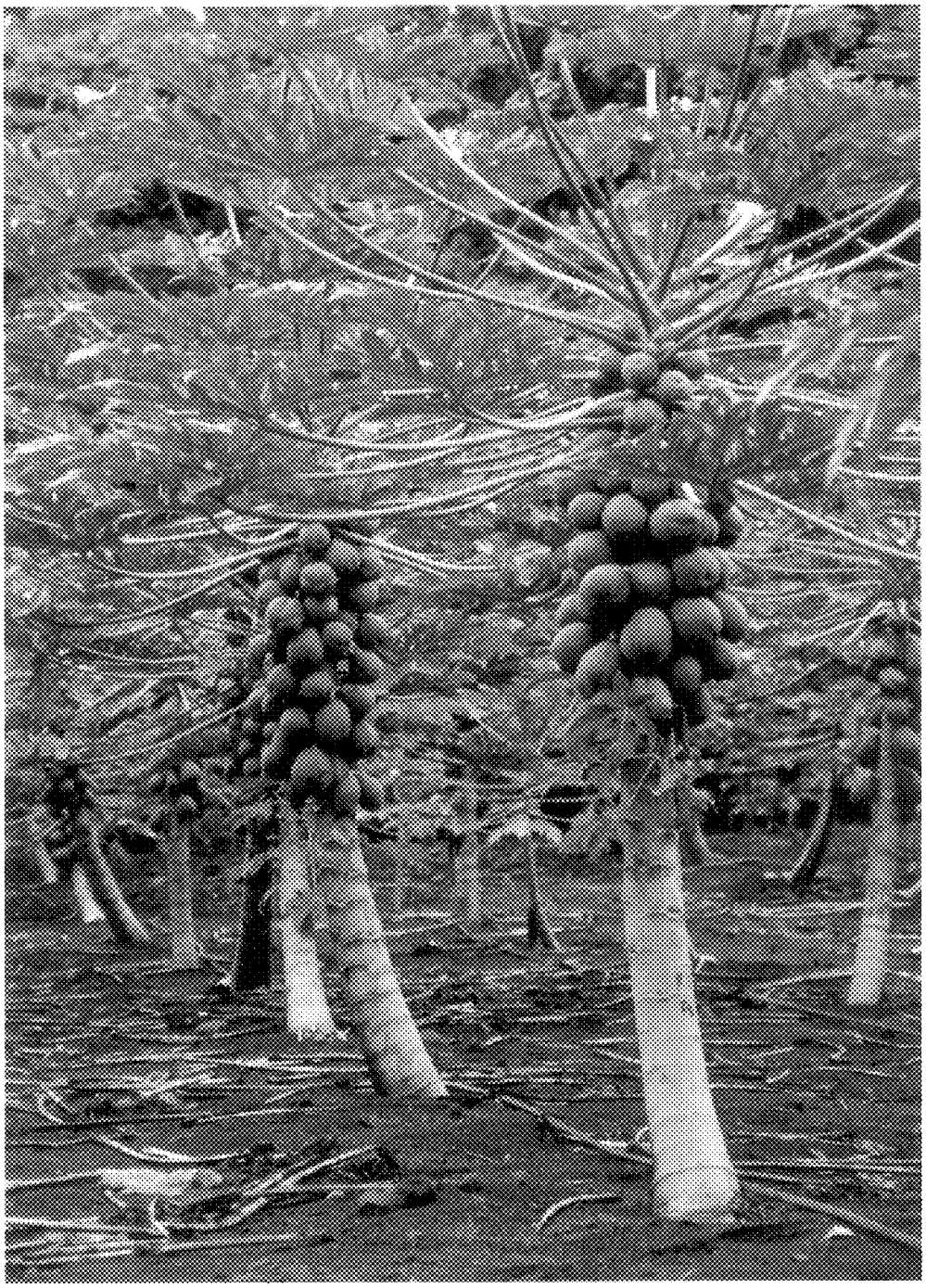
FIG. 1 shows the new variety just prior to the first fruit harvest, and is as representative as possible of the vegetative characteristics and of the fruit column free of carpellody and gaps due to sterility.
Figure 2:
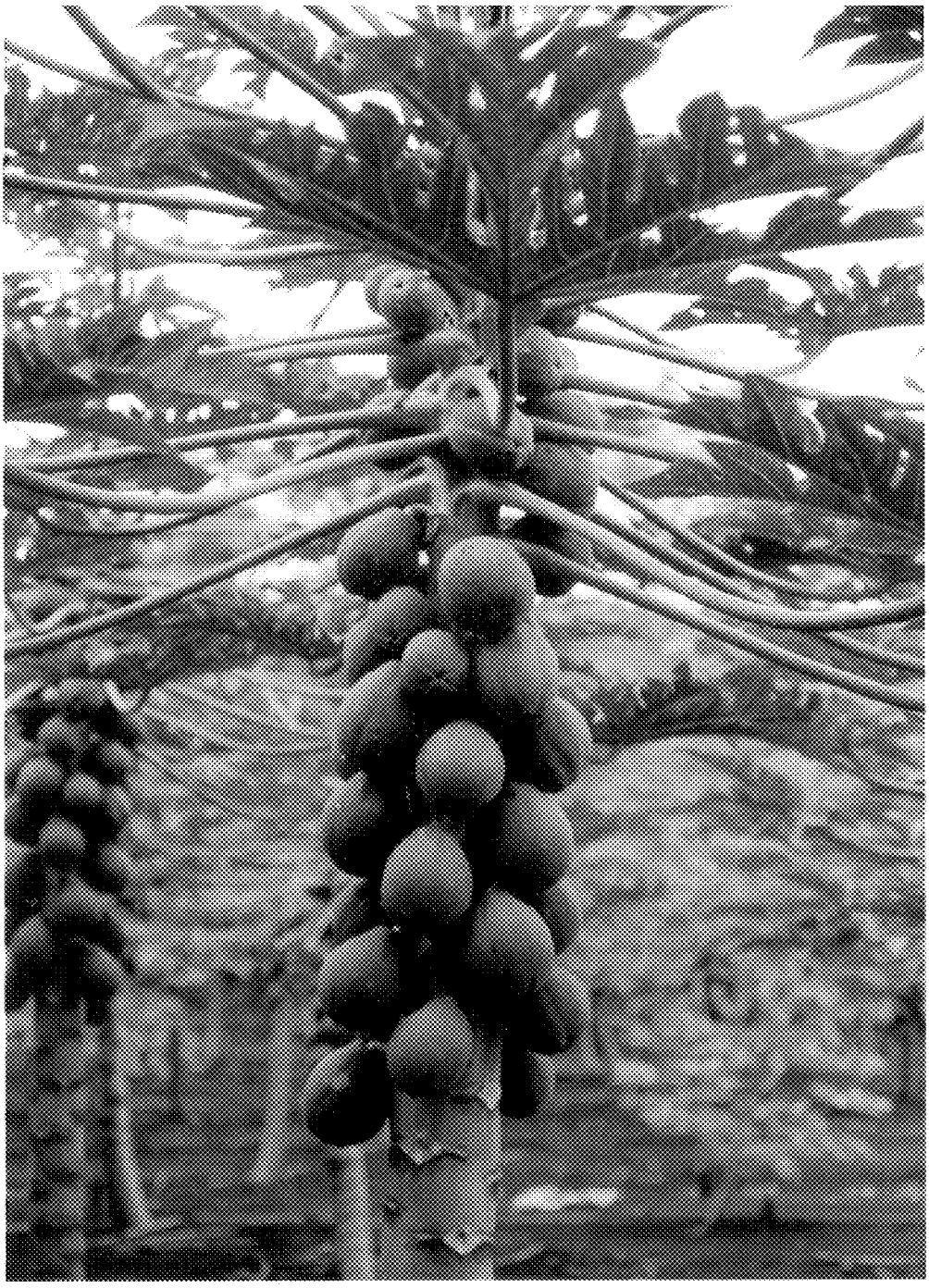
FIG. 2 is a close up showing the typical first fruits of the new variety just prior to the first fruit harvest.
Figure 3:
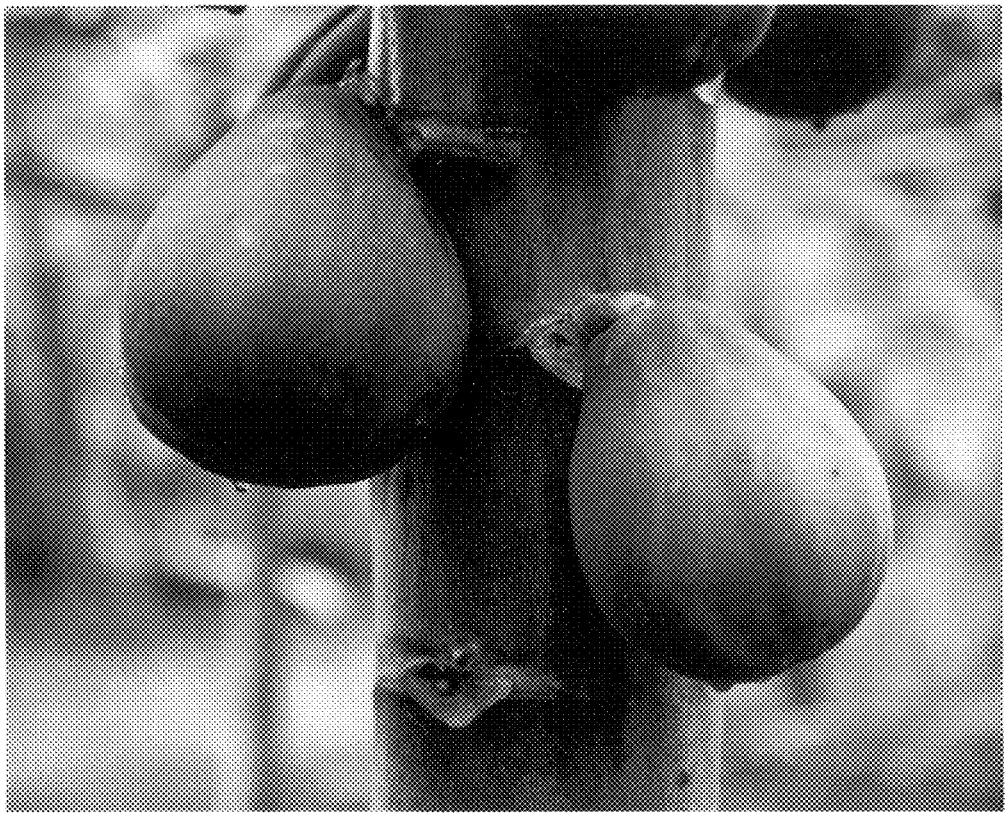
FIG. 3 shows the characteristic globular, pyriform fruits at the proper stage of ripeness for harvest.
Figure 4:
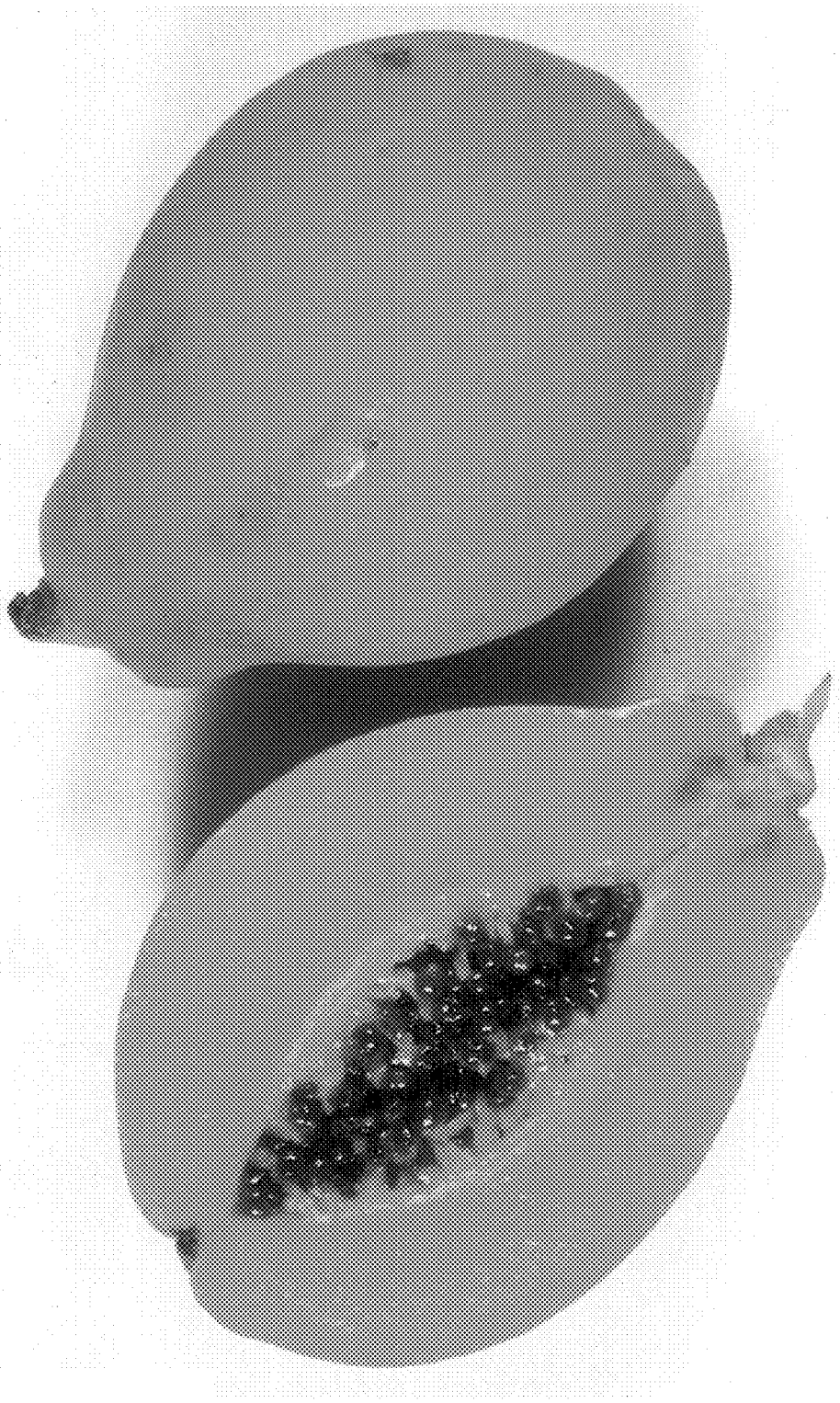
FIG. 4 shows fully ripe mature fruits, one of which has been sectioned to demonstrate the typical seed cavity form and flesh coloration, and the other is uncut to show typical ripe fruit skin color.

The new variety of papaya is most similar to the commercial papaya variety 'Kamiya' by having similar dates of flowering and harvesting, low bearing height, similar flesh color and thickness, total soluble solids, and flesh firmness, and fungus and nematode tolerance. It is distinguished therefrom and an improvement thereon in a number of fruit and tree characteristics, such as larger fruit size, increased tree vigor, PRSV resistance, absence of occasional bitterness and an unpleasant, strong odor during the cooler season, lower incidence of carpellody (a low temperature response wherein the stamens and carpels fuse and form a disfigured, unmarketable fruit) and lower incidence of sterility. Prior to the new variety, papaya fruit from 'Kamiya' plants were the largest of the standard "solo"-type fruit marketed in Hawaii. "Solo" refers to a papaya approximately 400–900 grams fresh weight, historically the size of papaya that could be consumed at one sitting by one person alone, or "solo" from the Portuguese language.

The new variety is similar to 'UH Rainbow' in having PRSV resistance and sweet, pleasant tasting fruit of moderate firmness. It is distinguished therefrom and an improvement thereon in having larger fruit size, increased tree vigor, increased fungus and nematode tolerance, and deeper orange flesh color.

The following is a detailed description of the new and distinct variety of papaya plant grown in the environments of Laie, Kahaluu, and Waikane, Hi. on the island of Oahu and is believed to apply to plants of the variety grown under similar conditions of soil and climate elsewhere. Where numeric values presented in the Detailed Description are followed by a "±" they represent the arithmetic mean plus or minus one standard error. In the following description, color references are made to The Royal Horticultural Society Colour Chart except where general terms of ordinary significance are used. Age is as given.

PLANT

Plant type: Arboreal monopodial.
Adaptation: Tropical lowland.
Maturity: 335 days from seeding to first harvest; 150 days from pollination to first harvest.
Size: Large, at 7 months after planting in Laie, Hi., 201±9 cm tall, 10.2±0.5 cm diameter.
Height at first harvest: 7 months after planting in Laie, Hi.: 201±9 cm.
Trunk diameter at first harvest, measured at 8 cm above the soil level at 7 months after planting in Laie, Hi.: 10.2±0.5 cm.
Width of the canopy at 7 months: 275.7±5.6 cm.
Plant gender: Gynodioecious, hermaphrodite trees.
Bark surface: Smooth.
Vigor: Vigorous.
Foliage density: 20–40 leaves at the apex.
Production: About 2–8 fruits/tree/week, for 52 weeks.
Bearer: Fruit productivity varies between years.
Bark texture: Smooth with protruding nodal scars.
Bark color, matured trunk, 60 cm above soil level: Greyed-green group 196C, young trunk (about 7 months old): Green group 136C.
Branches: (Evaluation from 1 cm diameter branches).
Branch texture: Smooth with protruding nodes.
Few branches form during the first year of growth; older trees develop 1–5 branches thereafter.
Shoot color of current season's growth from shoots ranging from 1–2 cm

LEAVES (Measurements were taken from fully mature leaves of current season growth.)

Size:
*Leaf lamina length 8 months after planting in Laie, Hi.*—71.2±1.4 cm.
*Leaf lamina width 8 months after planting in Laie, Hi.*—66.8±0.9 cm.
*Form.*—Shallowly lobed palmate.
*Number of lobes per leaf.*—9.
*Apex.*—Acuminate.
*Base.*—Cordate.
*Texture, adaxial surface.*—Smooth.
*Texture, abaxial surface.*—Moderately textured due to the raised veins having net-like or reticulated patterns.
*Margin.*—Smooth shallowly lobed, slightly wavy.
*Color.*—Upper surface glabrous: Green group 137A. Lower surface: Green group 137C.
*Leaf venation pattern of the adaxial leaf surface.*—Each of the 9 lobes contains a major vein with alternating minor veins radiating from the major vein.
*Leaf vein color, adaxial surface.*—Ranges from red group 50C to greyed-white group 156B.
*Leaf venation pattern of the abaxial leaf surface.*—Each of the 9 lobes contains a major vein with alternating minor veins radiating from the major vein. The veins viewed from the adaxial are smooth but are raised in a textured pattern on the abaxial surface and therefore appear more pronounced.
*Leaf vein color, abaxial surface.*—Yellow-green group 144B.
*Petiole.*—Yellow-green group 144C near lamina for most of the petiole surface, especially the abaxial surface, but adaxial surface also infused with light purple coloration (greyed-purple group 186D) generally extends into the leaf midrib as well as into the major secondary veins of the leaves.
*Petiole length 8 months after planting.*—98.2±1.3 cm.
*Petiole diameter 8 months after planting.*—1.7±0.05 cm.

FLOWERS

Flower buds, staminate:
*Size.*—3.4±0.07 cm long, 1–2 days pre-anthesis.
*Form.*—Bud consists of 5 coalescent petals that form a salverform corolla tube.
*Diameter of corolla tube 1 cm above the sepals, 1–2 days pre-anthesis.*—5.6±0.07 mm.

*Diameter of unopened free petals, 1–2 days pre-anthesis.*—8.1±0.08 mm.

Flower buds, hermaphrodite:

*Size.*—3.8±0.08 cm long, 1–2 days pre-anthesis.

*Form.*—Bud consists of 5 coalescent petals that form a swollen salverform corolla tube due to the presence of a functional ovary.

*Diameter of corolla tube at the widest part, 1–2 days pre-anthesis.*—1.5±0.09 cm.

*Diameter of the hermaphrodite bud, unopened free petals.*—1.35±0.02 cm.

Bud color, staminate and hermaphrodite: Yellow group 4D, 1–2 days pre-anthesis.

Flowers:

*Blooming period.*—Abundant year-round.

*Typical and observed flower types.*—Hermaphrodite papaya trees produce 3 types of flowers, staminate with functional anthers and abortive ovaries, perfect flowers with functional anthers and ovaries, and, occasionally, carpellodic flowers that resemble pistillate flowers with a 5-carpelled ovary and a variable number of stames up to five that sometimes fuse with the carpel and result in misshapen fruit.

*Size.*—Small to average, 1.9–3.4 cm diameter×3.8–5.7 cm long.

*Flower fragrance.*—A combination of ginger and jasmine.

*Flower number per node.*—One, two, or three types of flowers are borne at each node depending on the age of the tree, season, and water, and nutritional status of the plant. Flowers are either solitary or clustered. When clustered, the inflorescence is a cyme consisting of 2–9 buds when the tree is up to about 18 months old, but 2–4 is the typical number on trees older than 2 years.

*Diameter of cyme including buds and flowers.*—10.4±1.2 cm.

Petals, staminate:

*Petal shape.*—Non-coalescent part: Simple oblong.

*Petal length.*—Non-coalescent part: 2.0±0.3 cm, typically 5 petals.

*Petal width.*—0.9±0.08 cm at the widest part.

*Petal apex.*—Rounded.

*Petal base.*—Narrower than widest part of width, 0.4±0.07 cm.

*Corolla base diameter.*—0.46±0.07 cm.

Petals. hermaphrodite:

*Petal shape.*—Non-coalescent part: Simple oblong.

*Petal length.*—Non-coalescent part: 2.4±0.08 cm, typically 5, fewer and shorter if the hermaphrodite flowers are carpellodic and misshapen.

*Petal width.*—1.1±0.06 cm at the widest part.

*Petal apex.*—Rounded.

*Petal base.*—Narrower than widest part of width, 0.6±0.07 cm.

*Corolla base diameter.*—1.1±0.08 cm.

*Petal margin, staminate and hermaphrodite.*—Simple, smooth.

*Petal texture, staminate and hermaphrodite.*—Smooth inner surface, smooth and waxy outer surface.

*Petal color, staminate and hermaphrodite, inner surface.*—Yellow group 11D.

*Petal color, staminate and hermaphrodite, outer surface.*—Yellow group 4D.

Sepals, staminate flowers:

*Sepal shape.*—Simple, wide at base, rounded at apex.

*Sepal number.*—5 with bases coalesced.

*Sepal length.*—2.0±0.06 mm.

*Sepal width at base.*—1.7±0.1 mm.

*Sepal apex.*—Acute.

*Sepal margin.*—Smooth.

*Sepal color, inner surface.*—Yellow-green group 145A.

*Sepal color, outer surface.*—Yellow-green group 145A.

Sepals, hermaphrodite flowers:

*Sepal shape.*—Simple, wide at base, rounded at apex.

*Sepal number.*—5 with bases coalesced.

*Sepal length.*—3.0±0.4 mm.

*Sepal width at base.*—4.1±0.1 mm.

*Sepal apex.*—Acute.

*Sepal margin.*—Smooth.

*Sepal color, inner surface.*—Yellow-green group 145A.

*Sepal color, outer surface.*—Yellow-green group 145A.

Stamens, staminate and hermaphrodite flowers:

*Stamen quantity.*—10.

*Stamen size, 1–2 days pre-anthesis.*—4.0–4.3 mm long, 0.8 mm diameter.

*Stamen filament color.*—Yellow-white group 158D.

*Anther quantity.*—10 with double sacs.

*Anther size.*—2.7±0.1 mm long.

*Anther color.*—Yellow-orange color group 20B.

*Pollen.*—Present in hermaphrodite and staminate flowers.

*Pollen color.*—Evaluated after screening and drying, within a glass vial: Yellow-white group 158C.

*Pollen quantity.*—Copious.

*Pollen size.*—Small.

Stigma, staminate flowers, 1–2 days pre-anthesis:

*Stigma quantity, staminate flower.*—1, undeveloped, no lobes.

*Stigma size.*—<0.1 mm in diameter and <0.2 mm long.

*Stigma color.*—Yellow-green group 154B.

*Style quantity.*—1.

*Style length.*—0.5±0.1 cm.

*Style color.*—Yellow-white group 158D.

*Ovary quantity, staminate flower.*—1, underdeveloped.

*Ovary size.*—1.3±0.04 mm diameter, 1.4±0.02 mm long.

*Ovary color.*—Yellow-green group 149C.

*Self-fertility.*—Hermaphrodite plants are self-fertile.

FRUIT

Maturity: 335 days from seeding to first harvest; 150 days from pollination to first harvest.

Date of first picking: Oct. 30, 1998.

Date of last picking: Oct. 18, 1999.

Size: The average fruit mass of 'Laie Gold' calculated on 19 fruits harvested between 11/98–10/99 was 830±10.1 g/fruit. Fruit mass at harvest can be manipulated by the degree of fruit thinning. For 'Kamiya' the average mass for 260 fruits from about 30 trees was 712.6±1 g in the same time period.

Form: Pyriform to globular.

Average number per peduncle: Single or double.

Shape: Pyriform with neck absent or short neck.

Surface: Smooth.

Fruit abscission: When overripe.

Base attached to peduncle: Generally flattened with 5-point star pattern on hermaphrodites.

Fruit apex shape: Rounded with a slight depression for the pistil point.

Pistil point: Slightly depressed.

Typical and observed fruit length: From 10-month-old plants: 11.6±0.4 cm.
Typical and observed fruit diameter: From clones of 10-month-old plants: 8.1±0.3 cm.
Typical and observed seed cavity length: From 10-month-old plants: 8.4±0.3 cm.
Typical and observed seed cavity width: From 10-month-old plants: 4.1±1.6 cm.
Seed cavity: Cross-sectional Shape: Five-to eight-armed star.
Stem: The peduncle is of average thickness (1.3±0.4 cm) and length (3.9–8.9 cm).
Stem (peduncle) color: Greyed-orange group 164C.
Skin:
*Astringency.*—Slight amount noted particularly in areas of extreme overcolor.
*Thickness.*—Thin, less than 1 mm thick.
*Texture.*—Average to gritty, medium firm to firm.
*Tenacity.*—Tenacious to flesh.
*Tendency to crack.*—Low.
*Pubescence.*—None.
*Color.*—Yellow-orange group 21A.
*Overcolor.*—Freckles and spots generally absent but occasionally present depending on the season. Some may be physiological, others may be pathogen-induced hypersensitivity reponses. Both 'Kamiya' and 'Laie Gold' tend to be blemish-free with proper fungicide treatment.
*Mottling color.*—Yellow-green group 152C.
*Freckles.*—Generally absent but when present, color is greyed-orange group 165B.
Flesh:
*Color.*—Yellow-orange group 21A.
*Juice.*—Yellow-orange group 21D.
*Texture.*—Smooth to grainy.
*Fibers.*—None except for vasculature that can be coarse.
*Ripens.*—Evenly over most of the fruit, but the stem end ripens last.
*Flavor.*—A tasteful balance between sugars, acids, and aromatics.
*Eating quality.*—Exceptionally high.
*Brix.*—12.7±0.04° Brix, the average for 19 fruits harvested 11/98–10/99.
*Acidity.*—Medium.
*Aroma.*—Ranges from moderately mango-like with coconut and ginger that are enhanced by higher sweetness to very mildly mango- or coconut-like.
*Bitterness.*—Not bitter.

SEEDS

Measurements were made from seeds taken from fruit having an average fruit mass of 0.800 kg.

Attachment: To parietal placenta.
Typical and observed number of seeds per fruit: About 800.
Size:
*Average mass.*—12.7±0.03 mg.
*Average width.*—2.2±0.03 mm.
*Average length.*—3 mm±0.06 mm.
*Average diameter.*—4.5 mm±0.03 mm.
*Apex.*—Gently pointed at an apical tip. Tip is prominent but not sharp.
*Base.*—Gently rounded, slightly flattened.
*Surface.*—Highly textured with parallel ridges (wings) along the longitudinal axis.
*Ridges.*—Corky.
*Tendency to split.*—None.
*Color.*—Brown group 200A.
*Kernel.*—From generally well-filled teardrop shape.
*Taste.*—Astringent.
*Viability.*—Viable for over 1 year when stored at 4° C.
*Winter hardiness of cultivar.*—Winter in Hawaii typically is about 5–10 degrees cooler than summer. The 'Laie Gold' cultivar continues to grow and produce fruit in winter at elevations up to about 150 m above sea level, although at a lower frequency and sweetness. At elevations over 300 m, the trees cease fruit production. At temperate zone elevations of 1000–1500 m, the trees will freeze.

DISEASE AND INSECT RESISTANCE

Papaya mosaic virus: Untested.
Papaya leaf distortion mosaic virus: Untested.
Papaya ringspot virus: Resistant.
Powdery mildew: Susceptible.
Phytophthora root rot: Tolerant.
Nematodes: Tolerant.
Use: Fresh market papaya for use in local markets as well as for long distance shipping.
Keeping quality: Good.

The present new variety of papaya tree, its flowers, foliage, and fruit herein described may vary in slight detail due to climatic, soil conditions, and cultural practices under which the variety may be grown; the present description is that of the variety grown under the ecological conditions prevailing in Windward (Kahaluu and Waikane) and Northern (Laie) Oahu, Hawaii.

What is claimed is:

1. A new and distinct variety of papaya plant, substantially as illustrated and described herein.

* * * * *